(12) United States Patent
Jeong et al.

(10) Patent No.: US 12,697,509 B2
(45) Date of Patent: Aug. 4, 2026

(54) TREATMENT APPARATUS AND METHOD FOR TREATING, INHIBITING AND PREVENTING INFLAMMATORY DISEASE BY USING ELECTROMAGNETIC WAVE

(71) Applicant: AweXome Ray, Inc., Anyang-si (KR)

(72) Inventors: Keun Soo Jeong, Seoul (KR); Se Hoon Gihm, Seongnam-si (KR); Hong Soo Choi, Seoul (KR); Kang Pa Lee, Pohang-si (KR); Su Ji Baek, Seoul (KR)

(73) Assignee: AweXome Ray, Inc., Anyang-si (KR)

( * ) Notice: Subject to any disclaimer, the term of this patent is extended or adjusted under 35 U.S.C. 154(b) by 1079 days.

(21) Appl. No.: 17/701,426

(22) Filed: Mar. 22, 2022

(65) Prior Publication Data

US 2022/0305293 A1 Sep. 29, 2022

(30) Foreign Application Priority Data

Mar. 23, 2021 (KR) ........................ 10-2021-0037565

(51) Int. Cl.
*A61N 5/10* (2006.01)
*A61N 5/06* (2006.01)
(52) U.S. Cl.
CPC ......... *A61N 5/1048* (2013.01); *A61N 5/0616* (2013.01); *A61N 5/103* (2013.01); *A61N 5/1045* (2013.01); *A61N 2005/0661* (2013.01); *A61N 2005/1074* (2013.01); *A61N 2005/1094* (2013.01)
(58) Field of Classification Search
CPC .................................................. A61N 2/00–12
See application file for complete search history.

(56) References Cited

U.S. PATENT DOCUMENTS

| | | | |
|---|---|---|---|
| 4,833,334 A | 5/1989 | Valy et al. | |
| 2001/0053907 A1 | 12/2001 | Ota | |
| 2003/0191459 A1 | 10/2003 | Ganz et al. | |
| 2005/0245819 A1 | 11/2005 | Kumakhov | |
| 2008/0089481 A1 | 4/2008 | Gertner | |
| 2008/0247510 A1* | 10/2008 | Gertner ................ | A61B 6/508 |
| | | | 378/65 |

(Continued)

FOREIGN PATENT DOCUMENTS

| | | |
|---|---|---|
| CN | 103446676 A | 12/2013 |
| CN | 108136195 A | 6/2018 |

(Continued)

OTHER PUBLICATIONS

Jiawei Yan et al. "Lipid Metabolism in Regulation of Macrophage Functions," Trends in 1 Cell Biology, vol. 30, Issue 12, pp. 979-989, Dec. 1, 2020.

*Primary Examiner* — Thaddeus B Cox
(74) *Attorney, Agent, or Firm* — SEED INTELLECTUAL PROPERTY LAW GROUP LLP

(57) ABSTRACT

An electromagnetic wave treatment apparatus for treating, inhibiting, or preventing an inflammatory disease of an object, an operating method thereof, and a method for treating, inhibiting, or preventing an inflammatory disease of an object using the same is provided. An electromagnetic wave for treating, inhibiting, or preventing an inflammatory disease of an object and a use thereof, and a method including irradiating the electromagnetic wave onto the object is provided.

18 Claims, 10 Drawing Sheets

(56)          References Cited

U.S. PATENT DOCUMENTS

| | | | |
|---|---|---|---|
| 2009/0003525 A1* | 1/2009 | Gertner | A61N 5/1077 |
| | | | 378/65 |
| 2009/0163898 A1 | 6/2009 | Gertner et al. | |
| 2010/0067658 A1 | 3/2010 | Gertner et al. | |
| 2010/0074400 A1 | 3/2010 | Sendai | |
| 2010/0311643 A1 | 12/2010 | Bevec et al. | |
| 2011/0051895 A1 | 3/2011 | Vogtmeier et al. | |
| 2012/0286692 A1* | 11/2012 | Beckmann | H01J 35/065 |
| | | | 315/307 |
| 2019/0126057 A1 | 5/2019 | Feldreich | |
| 2019/0175938 A1 | 6/2019 | Rezaie et al. | |
| 2019/0255358 A1 | 8/2019 | Hale et al. | |
| 2021/0370317 A1 | 12/2021 | Choi et al. | |
| 2022/0080045 A1 | 3/2022 | Walder et al. | |

FOREIGN PATENT DOCUMENTS

| | | | | | |
|---|---|---|---|---|---|
| JP | 62-255893 A | 11/1987 | | | |
| JP | 2002-000745 A | 1/2002 | | | |
| JP | 2004-501730 A | 1/2004 | | | |
| JP | 2009-039414 A | 2/2009 | | | |
| JP | 2010-075338 A | 4/2010 | | | |
| JP | 2010-538986 A | 12/2010 | | | |
| JP | 2011-520233 A | 7/2011 | | | |
| JP | 2012-147866 A | 8/2012 | | | |
| JP | 2015-226576 A | 12/2015 | | | |
| JP | 2019-510074 A | 4/2019 | | | |
| JP | 2019-141581 A | 8/2019 | | | |
| JP | 2019-523687 A | 8/2019 | | | |
| JP | 2020048811 A | 4/2020 | | | |
| KR | 20060015567 A | 2/2006 | | | |
| KR | 10-2009-0080976 A | 7/2009 | | | |
| KR | 10-0910942 B1 | 8/2009 | | | |
| KR | 10-2012-0051478 A | 5/2012 | | | |
| KR | 20120043179 A | 5/2012 | | | |
| KR | 10-2013-0082364 A | 7/2013 | | | |
| KR | 20140099509 A | 8/2014 | | | |
| KR | 10-2017-0081120 A | 7/2017 | | | |
| KR | 10-2019-0015357 A | 2/2019 | | | |
| KR | 101992745 B1 * | 6/2019 | | .......... | H01J 35/065 |
| KR | 10-2019-0103736 A | 9/2019 | | | |
| KR | 10-2020-0114767 A | 10/2020 | | | |
| TW | 201811394 A | 4/2018 | | | |

* cited by examiner

Inflammation-
Induced
+ X-ray

Inflammation-
induced

Normal

TREATMENT APPARATUS AND METHOD FOR TREATING, INHIBITING AND PREVENTING INFLAMMATORY DISEASE BY USING ELECTROMAGNETIC WAVE

BACKGROUND

Technical Field

The present disclosure relates to an electromagnetic wave treatment apparatus for treating, inhibiting, or preventing an inflammatory disease of an object, an operating method thereof, and a method for treating, inhibiting, or preventing an inflammatory disease of an object using the same. The present disclosure also relates to an electromagnetic wave for treating, inhibiting, or preventing an inflammatory disease of an object and a use thereof, and a method including irradiating the electromagnetic wave onto the object.

Description of the Related Art

Electromagnetic waves include gamma rays, X-rays, ultraviolet (UV) rays, visible light, infrared (IR) rays, microwaves, and the like and are used in many industrial, scientific, and medical fields including communications and electronic fields. Electromagnetic waves in the IR and visible ranges are generally generated from an electrical energy source, which heats a material at a high temperature, and are used as light sources for heating, remote control, and lighting. Electromagnetic waves in the UV range are generally generated by heating gas through an electrical discharge and used in fields such as sterilization and polymer crosslinking.

The X-rays or gamma rays are used for identifying a part, which may not be confirmed by the naked eye, in various industrial fields such as medical, food, water purification, and security. In addition, the X-rays or gamma rays may also be used for treating by killing cancer cells or the like using high-energy characteristics of X-rays or gamma rays, and such a treatment method is classified into external radiotherapy (known as "teletherapy") in which radiation is irradiated into a human body and a brachytherapy in which an electromagnetic wave source is installed around an affected part and a treatment is performed.

A treatment method in the related art using an electromagnetic wave, in which high energy is applied to kill cells having a disease, has an advantage of exhibiting an excellent effect than treatment methods in the related art such as chemotherapy and the like but also involves the matter of causing side effects to a patient because normal cells in the vicinity of the cells having a disease are also killed.

Meanwhile, inflammation is expressed by the action of a normal in vivo defense mechanism, which appears locally against tissue damage caused by physical trauma, harmful chemicals, infections, and irritants in vivo metabolites. Such inflammation is known to recover a normal in vivo structure and function in normal cases, but may otherwise proceed to a disease state, such as chronic inflammation, and recently, many diseases are known to be caused by matters related to in vivo inflammatory response. Although various chemical therapies are used to treat such inflammatory diseases, there are many cases involving side effects, and there are many cases relieving symptoms temporarily.

BRIEF SUMMARY

An aspect provides an electromagnetic wave treatment apparatus for treating, inhibiting, or preventing an inflammatory disease of an object by irradiating the object with an electromagnetic wave having a wavelength of 0.05 nm or more and 10 nm or less, which may solve the technical matters as described above, an operating method thereof, and a treatment method using the same.

An aspect also provides an electromagnetic wave having a wavelength of 0.05 nm or more and 10 nm or less for treating, inhibiting, or preventing an inflammatory disease of an object, a use thereof, and a method of irradiating the electromagnetic wave onto the object.

According to an aspect, there is provided an electromagnetic wave treatment apparatus for treating, inhibiting, or preventing an inflammatory disease of an object.

The electromagnetic wave treatment apparatus for treating, inhibiting, or preventing an inflammatory disease of an object includes a power supplier, an irradiator configured to receive power from the power supplier and irradiate the object with an electromagnetic wave having a wavelength of 0.05 nm or more and 10 nm or less, and a controller configured to adjust a wavelength or dose of the electromagnetic wave irradiated from the irradiator.

The electromagnetic wave treatment apparatus may further include a filter configured to block the electromagnetic wave, which has a wavelength of less than 0.05 nm, from the irradiator.

The electromagnetic wave treatment apparatus may further include a protector that surrounds at least a portion of the irradiator.

The electromagnetic wave treatment apparatus may further include a distance measurer configured to measure a distance (L, meter) between a distal end of the irradiator and the object, and a position adjuster configured to adjust the distance between the distal end of the irradiator and the object. The controller may adjust the distance between the distal end of the irradiator and the object by controlling the position adjuster on the basis of the distance measured by the distance measurer.

The electromagnetic wave treatment apparatus may further include a collimator configured to adjust an irradiation range or intensity of the electromagnetic wave, and the collimator may be controlled by the controller.

The controller controls a voltage or a current supplied to the irradiator from the power supplier.

The electromagnetic wave treatment apparatus may further include a monitoring device configured to display a signal output from the controller.

The controller may control a dose of the electromagnetic wave absorbed by the object to be satisfied by adjusting at least one of the distance (L, meter) between the distal end of the irradiator and the object, an irradiation time (t, seconds), and an output voltage (V, voltage) or an output current (I, ampere) of the irradiator.

The electromagnetic wave treatment apparatus may be an apparatus that directly irradiates an electromagnetic wave onto a skin or into a body of the object or may further include an applicator connected to the irradiator so that the electromagnetic wave generated by the irradiator is directly irradiated into the body of the object.

The irradiator may correspond to a tube including an anode and a cathode, the anode may be connected to one side of the power supplier, and the cathode may be connected to the other side of the power supplier. The tube may further include at least one gate, and at least one of one side or the other side of the controller may be connected to the at least one gate. The cathode may include a carbon nanotube (CNT), the cathode may be formed of a CNT structure including a plurality of unit yarns each having a structure in which a plurality of CNTs are aggregated and extend in a first direction, and the CNT structure may be a structure in which a front end of each of the unit yarns faces the same direction as the first direction.

The inflammatory disease of the object may be a disease or lipid storage disorder mediated by a biomarker including at least one of interleukin (IL)-1β, IL-6, and tumor necrosis factor (TNF)-α, and the lipid storage disorder may include Niemann-Pick disease types A, B, and C; Gaucher disease type II; Fabry disease; gangliosidosis; Tay-Sachs disease; Sandhoff's disease; Krabe's disease; or metachromatic leukodystrophy, hepatitis, liver cancer, cirrhosis, nonalcoholic fatty liver or cholesteryl ester storage disease, and Ballman's disease.

At least one of the following indicators measured in the object may be measured higher than in the case of normal, and after the electromagnetic wave is irradiated onto the object, at least one of the following indicators measured in the object may be reduced:

Expression level of IL-1β in blood;

Expression level of IL-6 in blood;

Expression level of TNF-α in blood;

Expression level of messenger ribonucleic acid (mRNA) expressing intracellular IL-1β;

Expression level of mRNA expressing intracellular IL-6;

Expression level of mRNA expressing intracellular TNF-α; and

Amount of intracellular lipid accumulation.

The inflammatory disease of the object may be an autoimmune disease or an autoinflammatory disease. The autoimmune disease may include age-related macular degeneration (AMD); inflammatory skin diseases, psoriasis, atopic dermatitis; systemic scleroderma, sclerosis; Crohn's disease, ulcerative colitis; respiratory distress syndrome, adult respiratory distress syndrome; acute respiratory distress syndrome (ARDS); dermatitis; meningitis; encephalitis; uveitis; colitis; glomerulonephritis; allergic conditions, eczema, asthma, T-cell infiltration, other conditions associated with a chronic inflammatory response; atherosclerosis; leukocyte adhesion deficiency; arthritis, rheumatoid arthritis, inflammatory arthritis, juvenile rheumatoid arthritis, osteoarthritis, psoriatic arthritis; systemic lupus erythematosus (SLE); lupus nephritis (LN); diabetes, type I diabetes, insulin dependent diabetes; multiple sclerosis; Raynaud's syndrome; autoimmune thyroiditis; allergic encephalomyelitis; Sjogren's syndrome, juvenile onset diabetes; tuberculosis; sarcoidosis; polymyositis; granulomatosis and vasculitis; immune responses associated with acute and delayed hypersensitivity mediated by cytokines and T-lymphocytes typically found in tuberculosis; pernicious anemia, Addison's disease; diseases associated with leukopedesisgraft; central nervous system inflammatory disorders; multiple organ injury syndrome; hemolytic anemia; cryoglobinemia, Coombs positive anemia; myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; ehcet disease; giant cell arteritis; immune complex nephritis; IgA nephropathy; IgM polyneuropathies; or immune thrombocytopenic purpura (ITP) or autoimmune thrombocytopenia. The autoinflammatory disease may include familial Mediterranean fever (FMF); TNF receptor-associated periodic syndrome (TRAPS); hyperimmunoglobulinemia D with periodic fever syndrome (HIDS); systemic juvenile onset idiopathic arthritis (still disease); catastrophic antiphospholipid syndrome (CAPS); familial cold autoinflammatory syndrome; Muckle-Wells syndrome; deficiency of interleukin 1 receptor (DIRA) antagonist; Neonatal onset multisystem inflammatory disease (NOMID); or chronic infantile neurologic cutaneous articular (CINCA) syndrome.

According to an aspect, there is provided a method of operating the above-described electromagnetic wave treatment apparatus for treating, inhibiting, or preventing an inflammatory disease of an object.

The method may include positioning the irradiator such that the electromagnetic wave is irradiated onto the object, and irradiating the electromagnetic wave onto the object from the irradiator.

The electromagnetic wave treatment apparatus may further include an applicator connected to the irradiator so that the electromagnetic wave generated by the irradiator is directly irradiated into a body of the object, and the method may include inserting the applicator into the body of the object, and irradiating the electromagnetic wave into the body of the object from the irradiator.

According to an aspect, there is provided a method for treating, inhibiting, or preventing an inflammatory disease of an object by using the above-described electromagnetic wave treatment apparatus for treating, inhibiting, or preventing an inflammatory disease of an object.

According to an aspect, there is provided an electromagnetic wave having a wavelength of 0.05 nm or more and 10 nm or less for treating, inhibiting, or preventing an inflammatory disease of an object, and a use thereof.

According to an aspect, there is provided a method for treating, inhibiting, or preventing an inflammatory disease of an object, including irradiating an electromagnetic wave having a wavelength of 0.05 nm or more and 10 nm or less onto the object.

The present disclosure allows an inflammatory disease to be effectively treated or inhibited, and also, prevented without causing side effects such as the death of normal cells, which occur in electromagnetic wave treatment in the related art, by irradiating an object with an electromagnetic wave having a wavelength of 0.05 nm or more and 10 nm or less, which is called a soft X-ray.

Effects of the present disclosure will not be limited to the above-mentioned effects and other unmentioned effects will be clearly understood by those skilled in the art from the following claims.

BRIEF DESCRIPTION OF THE SEVERAL VIEWS OF THE DRAWINGS

FIG. 4B is a graph obtained by quantifying and comparing the amount of intracellular lipid accumulation.

DETAILED DESCRIPTION

Figure 1:
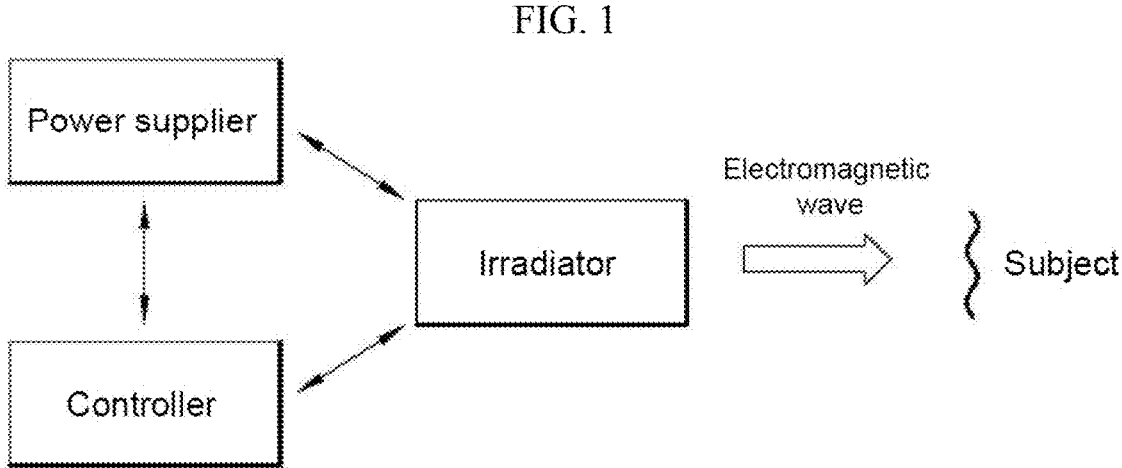
FIG. 1 is a schematic view illustrating main components of an apparatus for irradiating an electromagnetic wave onto an object, according to an example embodiment.

Hereinafter, the intent, operation, and effect of the present disclosure will be described in detail through the detailed description with reference to examples and drawings for helping the understanding of the example embodiments of the present disclosure. However, the following description and examples are presented as examples to help the understanding of the present disclosure as described above, and thus the scope of the present disclosure is not limited thereto.

Before describing the present disclosure in detail, the terms and words used in the present specification and claims should not be construed as limited to general or dictionary terms and should be interpreted with the meaning and concept in accordance with the technical spirit of the present disclosure on the basis of the principle that the inventors may adequately define the concept of a term in order to explain the disclosure in the best way.

Therefore, it should be understood that configurations of the example embodiments described herein are merely the most preferred embodiments of the present disclosure and are not representative of the full the technical spirit of the present disclosure, and various changes and modifications may be made at the time of filing the present application.

As used herein, singular forms are intended to include plural forms as well, unless the context clearly indicates otherwise. It should be understood that the terms "comprises," "comprising," "includes," "including," "contains," "including," "has," and/or "having," when used herein, specify the presence of stated features, integers, steps, operations, elements, components and/or combinations thereof, but do not preclude the presence or addition of at least one other features, integers, steps, operations, elements, components and/or combinations thereof.

As used herein, the terms " . . . er(or)," " . . . part," and the like refer to a unit that processes at least one function or operation, which may be implemented in hardware or software or implemented in a combination of hardware and software.

As used herein, the term "object" refers to, but is not limited to, humans or non-human mammals, such as cattle, horses, dogs, sheep, or cats, or parts thereof and includes a specific part to be irradiated with an electromagnetic wave by an electromagnetic wave treatment apparatus of the present disclosure. Preferably, the object is a human being or a part of a human body, and is a specific part to be irradiated with an electromagnetic wave by the electromagnetic wave treatment apparatus of the present disclosure.

As used herein, the terms "treatment," "treating," "treat," "inhibition," "inhibiting," and "inhibit" refer to a therapeutic treatment, the purpose of which is to slow the growth, development, or spread of an undesirable physiological change or disorder, for example, an inflammatory disease. For the purpose of the present disclosure, beneficial or desirable therapeutic or inhibitory effects include preventing the occurrence or recurrence of a disease, alleviating a symptom of the disease, diminishing any direct or indirect pathological consequences of the disease, preventing metastasis, decreasing the rate of disease progression, ameliorating or palliating the disease state, and achieving improved prognosis. In some embodiments, an electromagnetic wave treatment apparatus and an electromagnetic wave are used to delay the occurrence of a disease or slow the progression of the disease.

As used herein, the terms "prevention," "preventing," and "prevent" refer to reducing the likelihood that an event may occur in an object, that is, the likelihood of the occurrence of an undesirable physiological change or disorder, for example, an inflammatory disease, may occur in the object, but it is not required that the likelihood of the occurrence of the event be removed 100%.

In describing the example embodiments, descriptions of technical contents that are well known in the technical field to which the present disclosure pertains and are not directly related to the present disclosure will be omitted. This is to more clearly convey the gist of the present disclosure by omitting unnecessary description. For the same reasons, some components of the accompanying drawings have been exaggerated, omitted, or schematically illustrated. In addition, the size of each component does not fully reflect the actual size.

In one embodiment of the present disclosure, an electromagnetic wave treatment apparatus for treating, inhibiting, or preventing an inflammatory disease of an object include a power supplier, an irradiator, and a controller.

The power supplier may supply power to the irradiator, and the power supplier may further supply the power to the controller. The power supplied by the power supplier may be direct current (DC) power or alternating current (AC) power. The power supplier may include a battery, such as a lithium-ion battery, a lithium polymer battery, and a lithium solid battery. For example, the power supplier may include at least one of a pulse-width-modulation (PWM) inverter, an insulation transformer, and a boosting circuit (a voltage multiplier circuit or a smoothing circuit), and in this case, DC power generated by the battery may be converted into AC power by the PWM inverter. In addition, the converted AC power may be boosted by the insulation transformer, and high-voltage AC power may be output by the boosting circuit. In one specific example, the power supplier may merely supply DC power.

The irradiator is electrically connected to the power supplier, receives power from the power supplier, and irradiates an object with an electromagnetic wave. In one specific example, the irradiator may receive power from the power supplier and irradiate the object with an electromagnetic wave having a specific wavelength, and may irradiate the object with an electromagnetic wave having a wavelength of 0.05 nm or more and 10 nm or less. However, the specific wavelength is not limited a wavelength of the electromagnetic wave generated from the irradiator, but may be limited to a specific wavelength of the electromagnetic wave before reaching the object by other components, such as a filter, which will be described below.

The controller may include at least one of a transceiver, a memory, and a processor. In one specific example, the power supplier and the irradiator may each include at least one of a transceiver, a memory, and a processor. The processor may perform at least one method to be described throughout the specification, and the memory may store information for performing at least one method to be described throughout the specification, and codes of a program executed by the processor may be stored in the memory. The memory may be a volatile memory or a non-volatile memory.

The wavelength or dose of the electromagnetic wave irradiated from the irradiator may be adjusted by the controller. For example, the controller may control the irradiator to irradiate the electromagnetic wave having a specific wavelength, specifically, a wavelength of 0.05 nm or more and 10 nm or less. In addition, the controller may control the irradiator to irradiate the electromagnetic wave with a specific dose, that is, a specific voltage and current. Alternatively, the controller may control an irradiation time of the electromagnetic wave irradiated from the irradiator.

In the present disclosure, the electromagnetic wave having a wavelength of 0.05 nm or more and 10 nm or less may correspond to a soft X-ray. Alternatively, in the present disclosure, the electromagnetic wave may correspond to a soft X-ray corresponding to the remainder other than a high-energy X-ray having a wavelength range of 0.01 nm or more and 0.05 nm or less among X-rays.

In one specific example, the electromagnetic wave treatment apparatus for treating, inhibiting, or preventing an inflammatory disease of an object of the present disclosure may include the power supplier, the irradiator configured to receive power from the power supplier and irradiate the object with an electromagnetic wave having a wavelength of 0.05 nm or more and 10 nm or less, and the controller configured to adjust a wavelength or dose of the electromagnetic wave irradiated from the irradiator.

In one embodiment of the present disclosure, the electromagnetic wave treatment apparatus for treating, inhibiting, or preventing an inflammatory disease of an object may further include a filter configured to block the electromagnetic wave having a wavelength of less than 0.05 nm among the electromagnetic wave irradiated by the irradiator. The electromagnetic wave irradiated by the irradiator may be adjusted to have merely a wavelength of 0.05 nm or more and 10 nm or less by the controller. Alternatively, the irradiator may be configured as an X-ray tube that irradiates merely an electromagnetic wave having a wavelength of 0.05 nm or more and 10 nm or less so that the electromagnetic wave having a wavelength of 0.05 nm or more and 10 nm or less may be irradiated onto the object. However, the electromagnetic wave irradiated from the irradiator is not restricted by the theoretical limit, but the electromagnetic wave irradiated from the irradiator is more likely to include an electromagnetic wave having a wavelength of less than 0.05 nm. When the electromagnetic wave having a wavelength of less than 0.05 nm is irradiated onto the object, treatment effects on the object may be sufficiently achieved by appropriately adjusting an irradiation time, a distance between the object and a distal end of the irradiator, an output voltage, a current, and the like, but side effects caused by the high-energy X-ray may likely occur. Thus, in one specific example, the electromagnetic wave treatment apparatus may further include a filter that blocks the electromagnetic wave having a wavelength of less than 0.05 nm. Here, the term "block" may be understood as including completely blocking the transmission of the corresponding electromagnetic wave, as well as reducing transmittance to the extent of reducing the occurrence of side effects. The type of the filter is not particularly limited and may be selected by those skilled in the art.

In one embodiment of the present disclosure, the electromagnetic wave treatment apparatus for treating, inhibiting, or preventing an inflammatory disease of an object may further include a protector configured to surround at least a portion of the irradiator. The protector may prevent the electromagnetic wave irradiated from the irradiator from being irradiated to the surrounding environment other than a direction toward the object or outside a specific portion of the object to be irradiated. The electromagnetic wave generated from the irradiator is an electromagnetic wave having a wavelength of 0.05 nm or more and 10 nm or less, that is, a soft X-ray, and may cause unexpected harm to the surrounding environment when being irradiated to the surrounding environment other than the direction toward the object. Since the above-described electromagnetic wave treatment apparatus includes the protector surrounding at least a portion of the irradiator, the above-described matter may be prevented by allowing the electromagnetic wave irradiated from the irradiator to be irradiated merely toward the object that is a target to be irradiated. In addition, at least a portion of the irradiator is surrounded by the protector so that the irradiator may be protected from physical, chemical, or optical impact due to the external environment.

In one specific example, the protector may include an insulating material, such as a polymer, but the present disclosure is not limited thereto. The protector may be formed by attaching an insulating film to surround at least a portion of the irradiator, or by covering at least a portion of the irradiator by spraying or coating a liquid or semi-liquid insulating material thereon. The protector may be formed to surround the entire side surface of the irradiator. A thickness of the protector is not particularly limited. The thickness of the protector may be determined in a range where the electromagnetic wave irradiated from the irradiator is not irradiated to the surrounding environment other than the direction toward the object.

In one specific example, the electromagnetic wave treatment apparatus may include the filter configured to block the electromagnetic wave having a wavelength of less than 0.05 nm among the electromagnetic wave emitted from the irradiator. The filter may be included in the irradiator or positioned at one end of the irradiator, or may be positioned at one end of the protector. However, the present disclosure is not limited thereto, and the position of the filter is sufficient as long as the filter is positioned between the irradiator and the object so that the electromagnetic wave having a wavelength of less than 0.05 nm among the electromagnetic wave irradiated from the irradiator is not transmitted to the object or is transmitted with reduced transmission power.

In one embodiment of the present disclosure, the electromagnetic wave treatment apparatus for treating, inhibiting, or preventing an inflammatory disease of an object may further include a distance measurer that may measure a distance L (m) between the object and the distal end of the irradiator. The distance measurer may use a method of measuring a distance using the characteristic in which an intensity ratio of irradiated light and reflected light appears as a function of a distance between the distal end of the irradiator and the object or a method of calculating time-of-flight in consideration of a speed of light and calculating the distance between the distal end of the irradiator and the object, but the present disclosure is not limited thereto, and those skilled in the art may select other configurations that may measure the distance.

Here, the distal end of the irradiator refers to an end portion from which an electromagnetic wave from the electromagnetic wave treatment apparatus is irradiated onto the object, and in principle, refers to the irradiator. However, when other components, for example, the protector, the filter, an applicator, and the like are present between the irradiator and the object in an electromagnetic wave propagation direction, the distal end of the irradiator refers to an end of the component closest to the object among the components, where the end of the component is positioned closest to the object.

The distance measurer may be present by coming into close contact with the irradiator or may be positioned to be spaced apart from the irradiator by a predetermined distance, but the present disclosure is not limited thereto, and it is sufficient when the distance measurer is present at a position at which the distance between the distal end of the irradiator and the object may be measured.

In one specific example, the electromagnetic wave treatment apparatus for treating, inhibiting, or preventing an inflammatory disease of an object may further include a position adjuster configured to adjust the distance between the distal end of the irradiator and the object. Specifically, the position adjuster, which adjusts the distance between the distal end of the irradiator and the object, may include a path part allowing the irradiator to move relative to the object. For example, the irradiator may adjust the distance to the object by changing a position thereof along the path part, for example, a guide rail, a groove, or the like, to relatively move with respect to the protector surrounding at least a portion of the irradiator, but the present disclosure is not limited thereto.

In one specific example, the controller may adjust the distance between the distal end of the irradiator and the object by controlling the position adjuster on the basis of the distance measured by the distance measurer. Specifically, after receiving distance data measured from the distance measurer, the controller may control the position adjuster to adjust the distance between the distal end of the irradiator and the object to a specific value in order to achieve a distance between the distal end of the irradiator and the object, which exhibits desired treatment effects. For example, the controller may adjust the distance between the distal end of the irradiator and the object by changing the position of the irradiator using a device that is connected to the position adjuster and may be selected by those skilled in the art, for example, but is not limited to, a motor, a piston, or the like.

The controller may apply the value, which is input to the controller, to an electromagnetic wave irradiation model using the distance to the object, irradiation time, output voltage, and current as variables, and then, control the position adjuster to maintain the distance to the object suitable for achieving the desired treatment effects. After applying the value input to the controller to the model, the controller may further control the irradiator or the power supplier to control the irradiation time, the output voltage, and the current to achieve the desired treatment effect.

In one embodiment of the present disclosure, the electromagnetic wave treatment apparatus for treating, inhibiting, or preventing an inflammatory disease of an object may further include a collimator configured to adjust an irradiation range or intensity of the electromagnetic wave. For example, the collimator may represent an optical item, that is, any element that refracts an electromagnetic wave or changes an angular distribution of the electromagnetic wave in at least one axis, affects a focus of the electromagnetic wave in at least one axis, or otherwise affects properties of the electromagnetic wave, and may include mirrors and other reflective surfaces, lenses, prisms, light guides, gratings, and the like, but the present disclosure is not limited thereto.

For example, the collimator may be controlled by the controller. Desired effects of treating, inhibiting, or preventing an inflammatory disease may be achieved by controlling the collimator through the controller to adjust the irradiation range or intensity of the electromagnetic wave for the object. In addition, the controller may apply the value input to the controller to the model and then control the collimator to achieve the desired treatment effects.

In one embodiment of the present disclosure, the controller of the electromagnetic wave treatment apparatus for treating, inhibiting, or preventing an inflammatory disease of an object may control a voltage or current that is supplied to the irradiator from the power supplier. Specifically, the controller may control at least one of whether an electromagnetic wave irradiated from the irradiator is irradiated, an irradiation time, an irradiation area, an irradiation wavelength, and an irradiation intensity by controlling the voltage or current supplied to the irradiator from the power supplier.

The electromagnetic wave treatment apparatus of the present disclosure may further include a monitoring device configured to display signals output from the controller. The signals output from the controller may be related to whether the voltage is applied from the power supplier to the irradiator, a voltage application time, a voltage, a current, a distance between the distal end of the irradiator and the object measured by the distance measurer, whether the position adjuster is operated, or the like, but the present disclosure is not limited thereto.

In one embodiment of the present disclosure, a dose of the electromagnetic wave absorbed by the object ranges from 1 to 100 mGy per one-time treatment. Specifically, the dose of the electromagnetic wave absorbed by the object may range from 1 to 50 mGy per one-time treatment, and more specifically, the dose of the electromagnetic wave absorbed by the object may range from 10 to 15 mGy per one-time treatment. As used herein, the term "one-time irradiation" means that an electromagnetic wave is continuously irradiated onto the object without interruption in time, and the term "one-time treatment" refers to a series of acts of irradiating an electromagnetic wave to the object, and may include one-time irradiation or multiple-time irradiation. When the dose of the electromagnetic wave absorbed by the object per one-time treatment or one-time irradiation is low, the electromagnetic wave treatment apparatus of the present disclosure does not sufficiently achieve the desired effect, and when the dose of the electromagnetic wave absorbed by the object per one-time treatment or one-time irradiation is too high, since the energy of the electromagnetic wave may be accumulated in the object, cytotoxic effects such as cell damage and death may occur, or side effects such as damage to the skin or the occurrence of cancer may occur, which are not preferable. The dose of electromagnetic wave absorbed by the object may be measured by measuring the dose of the electromagnetic wave directly absorbed by the object, an electromagnetic wave dosimeter may be further included at one end of the irradiator or at a position spaced a certain distance from the irradiator, or the dose of the electromagnetic wave may be calculated from a function of the distance between the distal end of the irradiator and the object, and the output voltage, current, and irradiation time of the electromagnetic wave from the irradiator. For example, when an electromagnetic wave is irradiated multiple times per one-time treatment as in the case of irradiating the electromagnetic wave twice or more while performing one-time treatment on the object with the electromagnetic wave, a dose of the electromagnetic wave at one-time irradiation may be made smaller to keep the dose of the electromagnetic wave absorbed by the object during the one-time treatment constant. To this end, the distance between the distal end of the irradiator and the object, the output voltage, current, and irradiation time of the electromagnetic wave from the irradiator may be adjusted.

In one specific example, the controller may control the dose of the electromagnetic wave absorbed by the object to be satisfied by adjusting at least one of a distance L (m) between the distal end of the irradiator and the object, an irradiation time t (seconds), and an output voltage V (V), an output current I (A), or an output power P (W) of the irradiator. In one specific example, the distance L (m) between the distal end of the irradiator and the object may range from $1\times10^{-6}$ m to 3 m, specifically from $1\times10^{-5}$ m to 2 m, and more specifically from $1\times10^{-3}$ m to 1 m. The output voltage V (V) of the irradiator may be range from $1\times10^{-3}$ kV to 50 kV, specifically from 0.01 kV to 40 kV, and more specifically from 0.1 kV to 25 kV. The output current I (A) of the irradiator may range from $1\times10^{-3}$ mA to 100 mA, specifically from $5\times10^{-3}$ mA to 70 mA, and more specifically from 0.01 mA to 50 mA. The output power P (W) of the irradiator may range from $1\times10^{-6}$ W to 5000 W, specifically from $5\times10^{-5}$ W to 2800 W, more specifically from $1\times10^{-3}$ W to 1000 W, and still more specifically from 1 W to 20 W. The irradiation time t (seconds) of the electromagnetic wave may range from 0.001 seconds to 1000 seconds, specifically from 0.005 seconds to 800 seconds, and more specifically from 0.01 seconds to 600 seconds. The dose of the electromagnetic wave absorbed by the object may be adjusted by changing the range of each of the distance L (m) between the distal end of the irradiator and the object, the irradiation time t (sec), and the output voltage V (V), the output current I (A), and the output power P (W) of the irradiator, and the desired dose of the electromagnetic wave may be determined through a combination of five indicators.

In one embodiment of the present disclosure, the electromagnetic wave irradiated from the electromagnetic wave treatment apparatus may be irradiated onto the object, specifically, a skin of the object. Here, the skin of the object may be an affected part in which an inflammatory disease occurs and a treatment or inhibition thereof is required or otherwise desired, a skin tissue in the vicinity of the affected part, or a skin that is expected to occur an inflammatory disease. In addition, when the electromagnetic wave is irradiated onto the skin of the object, the inflammatory disease occurred in the object may be occurred at a part other than the skin onto which the electromagnetic wave is irradiated. For example, when an inflammatory disease occurs in a joint, the electromagnetic wave may be irradiated onto a skin of the joint part of the object or an arbitrary part of the object.

Further, the electromagnetic wave irradiated from the electromagnetic wave treatment apparatus may be an electromagnetic wave directly irradiated into the body of the object. Here, when the electromagnetic wave is directly irradiated into the body of the object, the electromagnetic wave may be directly irradiated onto the affected part in which an inflammatory disease occurs and a treatment or inhibition thereof is required or otherwise desired, a part that is expected to occur an inflammatory disease, or a part of the body other than the part in which the inflammatory disease has occurred.

As such, the part of the object, onto which the electromagnetic wave is irradiated, may be a skin or a part in the body, and may be an affected part or a part other than the affected part.

In one embodiment of the present disclosure, the electromagnetic wave treatment apparatus may further include an applicator connected to the irradiator so that an electromagnetic wave generated by the irradiator may be irradiated directly into the body of the object. For example, the applicator may be configured in the form of a tube designed to be inserted directly into the body of the object, such as in the form of an optical fiber, so that electromagnetic wave generated from the irradiator may be irradiated into the body of the object along a path formed on an inner surface of the applicator. Alternatively, the irradiator may be directly inserted into the body of the object by being surrounded by the applicator, and the electromagnetic wave irradiated from the irradiator may be directly irradiated into the body of the object through the applicator. However, the applicator is not limited to the above example, and those skilled in the art may select a configuration in which the electromagnetic wave generated by the irradiator may be directly irradiated into the body of the object. In one embodiment of the present disclosure, the irradiator may include a tube including an anode and a cathode. In this case, the anode may be connected to one side of the power supplier and the cathode may be connected to the other side of the power supplier so that power from the power supplier may be supplied to the tube including the anode and the cathode. In one specific example, the tube including the anode and the cathode may further include at least one gate, and at least one of one side or the other side of the controller may be connected to the at least one gate. The gate may be one of a grid, a wire, or a gate of a pin-hole structure. In addition, the gate may also be formed of one or more wires and one or more empty spaces. In a case in which the gate is present in the tube, the gate may be formed of one gate, and may be a multi-gate formed of a plurality of gates. The gate may induce the emission of electrons, and the electrons may be emitted from the cathode on the basis of a voltage applied to the tube.

In one specific example, the cathode may include a carbon nanotube (CNT). Specifically, the cathode may correspond to an emitter formed of a CNT. In this case, a field emission element of the cathode, that is, the emitter, may be formed of a CNT structure including a plurality of unit yarns each having a structure in which a plurality of CNTs are aggregated and extend in a first direction. In this case, the CNT structure may be designed such that a front end of each of the unit yarns faces the same direction as the first direction. In the case of the tube designed in this way, it is advantageous in that most of electrons emitted through the front end of the structure may be emitted in the first direction, which is a direction in which each CNT and unit yarn extend. Thus, it is advantageous in that, when the tube is applied to an X-ray tube that generates X-rays through collisions of a metal target and electrons, most of the electrons may be concentrated to the desired collision portion.

However, this is merely an example of configuring the irradiator, and the irradiator does not necessarily include the cathode corresponding to the emitter composed of CNTs, and, as described above, the irradiator may irradiate an electromagnetic wave in a wavelength range of 0.05 nm or more and 10 nm or less, and may also irradiate an electromagnetic wave of wavelengths outside the above range, but the electromagnetic wave of wavelengths outside the above range may be blocked by the configuration that further includes the above-described filter.

In one embodiment of the present disclosure, an inflammatory disease of the object which is treated, inhibited, or prevented by the electromagnetic wave treatment apparatus may be a disease mediated by a biomarker. The biomarker refers to any in vivo material that mediates an inflammatory metabolic reaction or causes an inflammatory disease in the object, and may specifically include interleukins (IL), tumor necrosis factors (TNF), or the like, and more specifically, may be at least one of IL-1$\beta$, IL-6, and TNF-$\alpha$, but the present disclosure is not limited thereto. In one embodiment of the present disclosure, an inflammatory disease of the object that is treated, inhibited or prevented by the electromagnetic wave treatment apparatus may be a lipid storage disorder.

In the present disclosure, the object whose inflammatory disease is treated, inhibited, or prevented by the electromagnetic wave treatment apparatus may be a target in which at least one of the following indicators measured in the object is measured higher than in the case of normal. In one specific example, at least one of the following indicators, which are measured from the object after the object is irradiated with an electromagnetic wave irradiated from the electromagnetic wave treatment apparatus according to the present disclosure, may be reduced in value than the following indicator measured before irradiating the electromagnetic wave:

Expression level of IL-1$\beta$ in blood;

Expression level of IL-6 in blood;

Expression level of TNF-$\alpha$ in blood;

Expression level of messenger ribonucleic acid (mRNA) expressing intracellular IL-1$\beta$;

Expression level of mRNA expressing intracellular IL-6;

Expression level of mRNA expressing intracellular TNF-$\alpha$; and

Amount of intracellular lipid accumulation.

Here, the "normal" may refer to a case in which the object is diagnosed as not having inflammatory diseases or the object is diagnosed as unlikely to occur inflammatory diseases.

In one embodiment of the present disclosure, the inflammatory diseases of the object which are treated, inhibited, or prevented by the electromagnetic wave treatment apparatus may be autoimmune diseases or autoinflammatory diseases. Specifically, the autoimmune diseases may include age-related macular degeneration (AMD); inflammatory skin diseases, psoriasis, atopic dermatitis; systemic scleroderma, sclerosis; Crohn's disease, ulcerative colitis; respiratory distress syndrome, adult respiratory distress syndrome; acute respiratory distress syndrome (ARDS); dermatitis; meningitis; encephalitis; uveitis; colitis; glomerulonephritis; allergic conditions, eczema, asthma, T-cell infiltration, other conditions associated with a chronic inflammatory response; atherosclerosis; leukocyte adhesion deficiency; arthritis, rheumatoid arthritis, inflammatory arthritis, juvenile rheumatoid arthritis, osteoarthritis, psoriatic arthritis; systemic lupus erythematosus (SLE); lupus nephritis (LN); diabetes, type I diabetes, insulin dependent diabetes; multiple sclerosis; Raynaud's syndrome; autoimmune thyroiditis; allergic encephalomyelitis; Sjogren's syndrome, juvenile onset diabetes; tuberculosis; sarcoidosis; polymyositis; granulomatosis and vasculitis; immune responses associated with acute and delayed hypersensitivity mediated by cytokines and T-lymphocytes typically found in tuberculosis; pernicious anemia, Addison's disease; diseases associated with leukopedesisgraft; central nervous system inflammatory disorders; multiple organ injury syndrome; hemolytic anemia; cryoglobinemia, Coombs positive anemia; myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; ehcet disease; giant cell arteritis; immune complex nephritis; IgA nephropathy; IgM polyneuropathies; and immune thrombocytopenic purpura (ITP) or autoimmune thrombocytopenia.

The immune-related and inflammatory diseases are responsive to injury or damage in normal physiological conditions, initiate recovery from injury or damage, and initiate innate and acquired defenses against foreign organisms and thus are symptoms or consequences of important, fairly complex, and often multiple interconnected biological pathways. The disease or pathology conditions are generated when these normal physiological paths are directly related to the intensity of the reaction, as a result of abnormal conditioning or excessive stimulation, as a result of itself, or as a combination thereof, causing further injury or damage.

The autoinflammatory diseases may include familial Mediterranean fever (FMF); TNF receptor-associated periodic syndrome (TRAPS); hyperimmunoglobulinemia D with periodic fever syndrome (HIDS); systemic juvenile onset idiopathic arthritis (still disease); catastrophic antiphospholipid syndrome (CAPS); familial cold autoinflammatory syndrome; Muckle-Wells syndrome; deficiency of interleukin 1 receptor (DIRA) antagonist; Neonatal onset multisystem inflammatory disease (NOMID); and chronic infantile neurologic cutaneous articular (CINCA) syndrome.

The lipid storage disorders may include Niemann-Pick disease types A, B, and C; Gaucher disease type II; Fabry disease; gangliosidosis; Tay-Sachs disease; Sandhoff s disease; Krabe's disease; and metachromatic leukodystrophy, hepatitis, liver cancer, cirrhosis, nonalcoholic fatty liver or cholesteryl ester storage disease, and Ballman's disease.

The electromagnetic wave treatment apparatus according to the present disclosure may be used together with a known inflammatory disease treating composition in order to treat, inhibit, or prevent an inflammatory disease of the object. Specifically, the inflammatory disease treating composition is administered to the object and then an electromagnetic wave is irradiated onto the object using the electromagnetic wave treatment apparatus according to the present disclosure so that the effect of treating the inflammatory disease may be further increased. Alternatively, the inflammatory disease treating composition is applied to an affected part of the object and then an electromagnetic wave is irradiated onto the object using the electromagnetic wave treatment apparatus according to the present disclosure so that the effect of treating the inflammatory disease may be further increased.

The present disclosure provides a method for operating the above-described electromagnetic wave treatment apparatus, and may include positioning an irradiator to irradiate an object with an electromagnetic wave and irradiating the object with the electromagnetic wave by the irradiator. In one specific example, the above-described electromagnetic wave treatment apparatus may further include an applicator connected to the irradiator such that the electromagnetic wave generated by the irradiator may be irradiated directly into a body of the object, and the method for operating the applicator may include inserting the applicator into the body of the object and irradiating the electromagnetic wave into the body of the object by the irradiator. Here, the applicator is as defined previously in the present specification.

The present disclosure provides a method for treating, inhibiting, or preventing an inflammatory disease of an object, including irradiating the object with an electromagnetic wave having a wavelength of 0.05 nm or more and 10 nm or less. In addition, the present disclosure provides a method for treating, inhibiting, or preventing an inflammatory disease of an object using the electromagnetic wave treatment apparatus described above. Further, the present disclosure provides an electromagnetic wave for treating, inhibiting, or preventing an inflammatory disease of an object with a wavelength of 0.05 nm or more and 10 nm or less, and a use thereof for treating, inhibiting, or preventing inflammatory diseases of an object.

EXAMPLES

Hereinafter, Examples will be described in detail so that the operation and effect of the present disclosure is demonstrated. However, the following Examples are merely illustrative of the disclosure and are not intended to limit the scope of the disclosure.

Example 1

Confirmation of Cell Viability According to Irradiation Time of Electromagnetic Wave The following experiment was conducted to confirm whether toxicity such as cell death exists when an electromagnetic wave having a wavelength of 0.05 nm or more and 10 nm or less was irradiated onto a cell.

RAW264.7 macrophage cells were incubated with Dulbecco's modified Eagles' Medium (DMEM) containing 10% fetal bovine serum (FBS) and 1% penicillin-streptomycin at 37+/−2° C. and in an atmosphere of 5% $CO_2$. The cells were seeded at $1 \times 10^4$ cell/well on a 96 well-plate. The cells were irradiated with an electromagnetic wave (wavelength of 0.05 nm or more and 10 nm, output power of 4.9 W at a distance of 0.07 m) for 5 minutes, 10 minutes, and 20 minutes, respectively, and then incubated at 37+/−2° C. for 24 hours. The cells were incubated with an XTT reagent at 37+/−2° C. for 2 hours, and then cell viability was measured at 450 nm using a microplate reader (Bio-Rad Laboratories, Hercules, Calif, USA).

Figure 2:
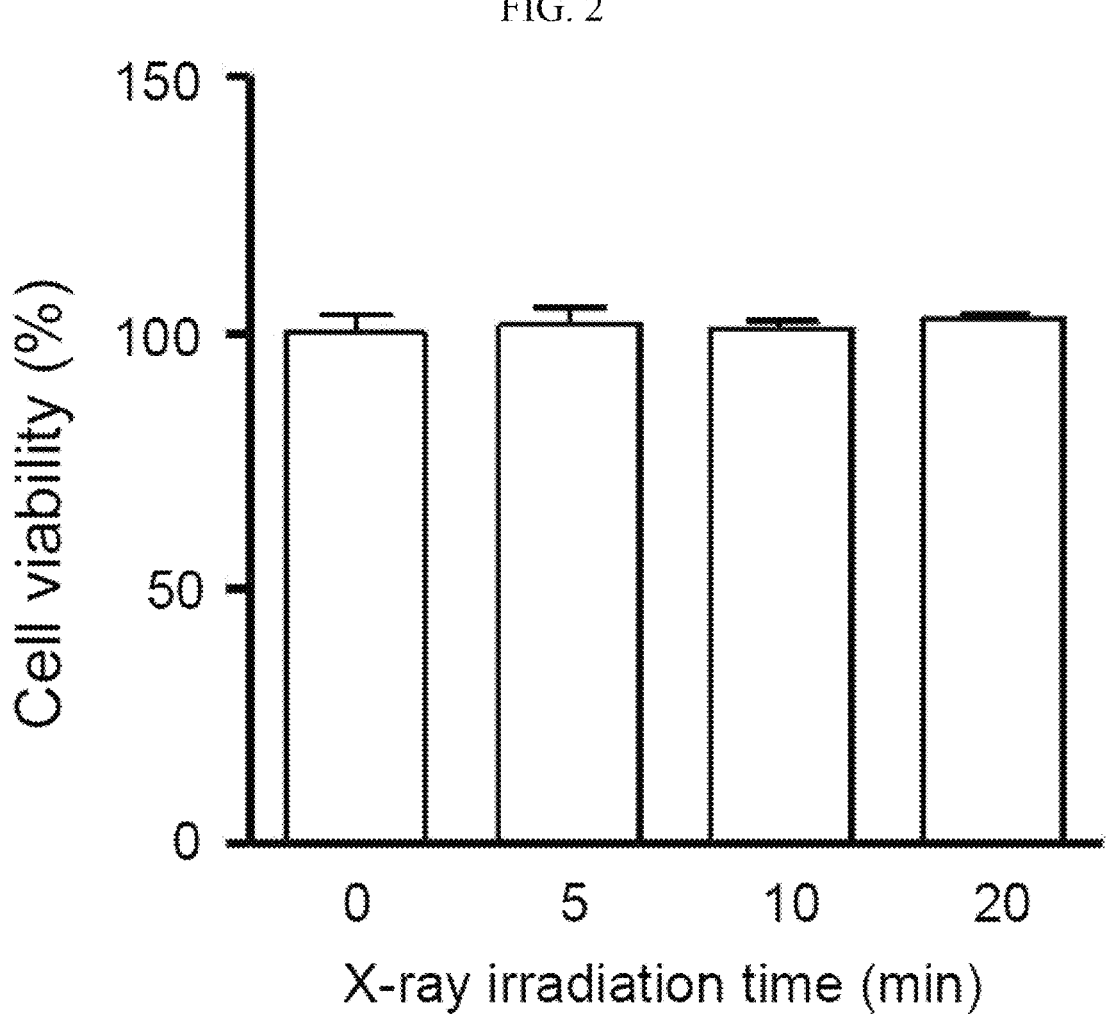
FIG. 2 is a graph confirming whether cytotoxicity occurs due to an electromagnetic wave having a wavelength of 0.05 nm or more and 10 nm or less by measuring cell viability, and illustrates whether cells survive when the cells are irradiated with the electromagnetic wave for 0, 5, 10, and 20 minutes and then incubated.

As a result, as shown in FIG. 2, it was confirmed that, when the RAW264.7 macrophage cells were irradiated with the electromagnetic wave having a wavelength of 0.05 nm or more and 10 nm or less at different irradiation times, there was no remarkable difference in cell viability as compared to RAW264.7 macrophage cells that were not irradiated with the electromagnetic wave. Accordingly, it was confirmed that even when the electromagnetic wave having a wavelength of 0.05 nm or more and 10 nm or less was irradiated onto the cells, cytotoxicity such as cell death or cell damage was not observed.

Example 2

Confirmation of Effect of Electromagnetic Wave on Inflammatory Response of LPS-Treated RAW264.7 Macrophage Cells The following experiment was conducted to confirm treatment effects on an inflammatory response through changes in a molecular level caused when an electromagnetic wave having a wavelength of 0.05 nm or more and 10 nm or less was irradiated onto the cells in which the inflammatory response was induced.

Western Blot

RAW264.7 macrophage cells were seeded at a density of $1 \times 10^5$ cells/well on a 6 well-plate, incubated for 24 hours, and then treated with 500 μM lipopolysaccharide (LPS) for 3 hours to induce an inflammatory response. The LPS-treated RAW264.7 macrophage cells were irradiated with an electromagnetic wave having a wavelength of 0.05 nm or more and 10 nm or less and an output power of 4.9 W at a distance of 0.07 M for 10 minutes, and then incubated at 37+/−2° C. and in an atmosphere of 5% $CO_2$ for 21 hours without further irradiation of the electromagnetic wave. In order to perform Western blotting, proteins were extracted from normal RAW264.7 macrophage cells, with which LPS was not treated, the LPS-treated RAW264.7 macrophage cells, and the RAW264.7 macrophage cells, which were irradiated with an electromagnetic wave after the LPS treatment was performed, and then the concentration of the extracted proteins was measured using a protein assay reagent (Bio-Rad, Hercules, Calif, USA). The extracted protein sample was mixed with a sodium dodecyl sulfate (SDS) buffer solution at a ratio of 1:1 and then heated for 10 minutes to transform the proteins. After 30 μg of the protein sample was loaded per column of 12% SDS-polyacrylamide gel electrophoresis (PAGE), the protein sample was separated through electrophoresis, and then electrically transferred to a polyvinylidene fluoride (PVDF) membrane (Millipore, Bedford, Mass., USA). The PVDF membrane was blocked by in phosphate buffered saline (PBS) solution containing 5% bovine serum albumin (BSA) at room temperature for 2 hours. The PVDF membrane was incubated with an anti-IL-1β antibody (1:1000) at 4° C. for 16 hours. The membrane was incubated with a horseradish peroxidase-conjugated secondary antibody for 1 hour. To detect the IL-1β, the membrane was incubated with an enhanced luminescence (ECL) reagent and the expression of IL-1β were detected using the chemiluminescence detector. The expression of IL-1β was analyzed using the ImageJ program.

Figure 3A:
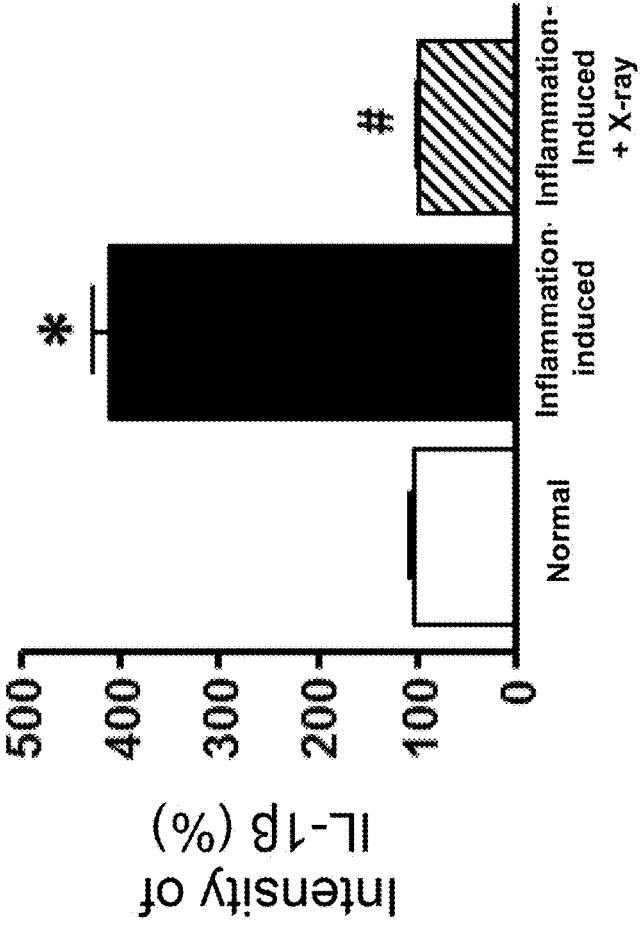
FIG. 3A illustrates a result of comparing expression levels of IL-1β protein, which is a cytokine that exhibits an inflammatory response, using Western blot for normal cells in which the inflammatory response is not induced, inflammation-induced cells in which the inflammatory response is induced, and cells in which an electromagnetic wave is irradiated onto the inflammation-induced cells in which the inflammatory response is induced, and a graph thereof.
Figure 3A:
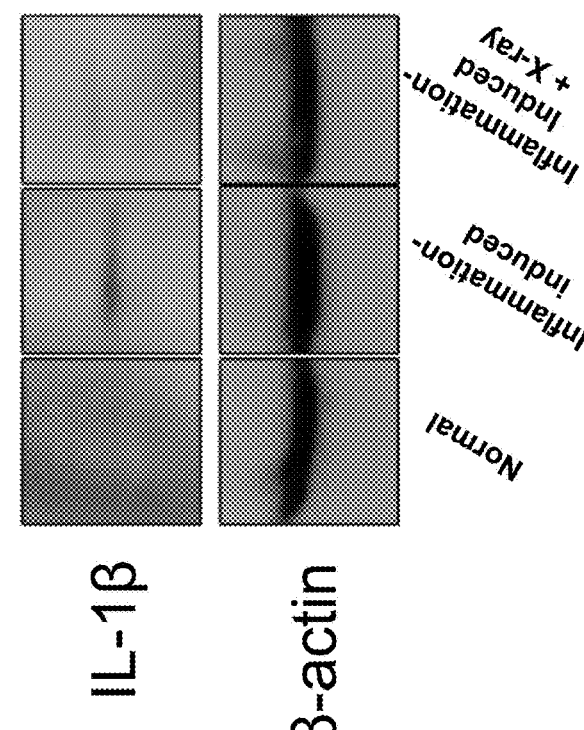
Figure 3B:
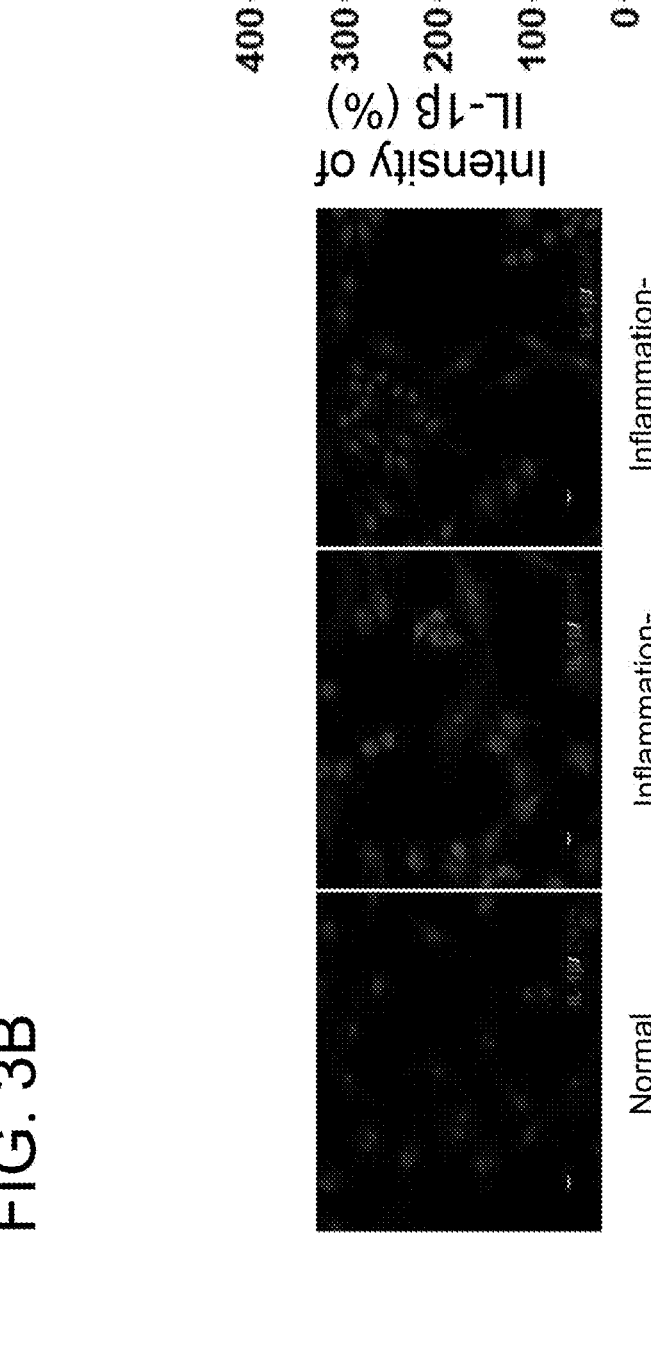
FIG. 3B illustrates a result of comparing expression levels of IL-1β protein using immunocytochemistry and fluorescence imaging and a graph thereof.

Western blot of IL-1β protein expression was confirmed from the normal RAW264.7 macrophage cells, the RAW264.7 macrophage cells, in which LPS was treated to induce an inflammatory response, and the RAW264.7 macrophage cells treated with the electromagnetic wave having a wavelength of 0.05 nm or more and 10 nm or less after the LPS treatment was performed (as shown in the left side in FIG. 3A, "Normal," "Inflammation induced," "Inflammation induced+X-ray" are illustrated in order). As a result of relative quantitative analysis of the expression level of IL-1β through image analysis of Western blot results, the expression level of IL-1β was increased by 329.8 (±17.1)% in the RAW264.7 macrophage cells, in which LPS was treated to induce an inflammatory response, as compared with the normal RAW264.7 macrophage cells. On the other hand, the expression level of IL-1β was reduced by 297.8(±14.2)% in the RAW264.7 macrophage cells, which were treated with the electromagnetic wave having a wavelength of 0.05 nm or more and 10 nm or less, as compared with the RAW264.7 macrophage cells in which the inflammatory response was induced, and thus remarkable inflammatory response reduction effect was exhibited, and there was no remarkable difference as compared with the normal cells. Accordingly, it was confirmed that, when the electromagnetic wave having a wavelength of 0.05 nm or more and 10 nm or less was irradiated onto the cells in which the inflammatory response was reduced, the expression of IL-1β protein was reduced, and as a result, it was confirmed that the electromagnetic wave having a wavelength of 0.05 nm or more and 10 nm or less has reduced the inflammatory response of the cell.

Immunocytochemistry

RAW264.7 macrophage cells were seeded in 8 chambers at 5×10³ cells/well. The cells were divided 3 groups following: normal RAW264.7 macrophage cells; the LPS-treated RAW264.7 macrophage cells; the RAW264.7 macrophage cells were irradiated with the electromagnetic wave after the LPS treatment. The cells were treated with 500 μM LPS for 3 hours. And the LPS-treated RAW264.7 macrophage cells were irradiated with an electromagnetic wave having a wavelength (0.05 nm or more and 10 nm or less and an output power of 4.9 W at a distance of 0.07 m) for 10 minutes, and then incubated at 37+/−2° C. and in an atmosphere of 5% $CO_2$ for 21 hours. The 3 groups cells were fixed with 4% formalin for 10 minutes and cell membranes were dissolved in a 0.1% Triton X-100 solution. The cells were incubated with an anti-IL-1β antibody for 1 hour and Alexa Fluor 488-conjugated secondary antibody (1:1000) for 1 hour at room temperature. Nucleuses were stained with 4',6-diamidino-2-phenylindole (excitation wavelength: 358 nm, and emission wavelength: 461 nm). Fluorescence images were obtained using a fluorescence microscope (K1-Fluo, Nanoscope System Co., Daejeon, Korea), and fluorescence intensities were measured and analyzed using the ImageJ.

As a result, as shown in FIG. 3, even in the analysis of IL-1β protein expression through immunocytochemical analysis, the expression of IL-1β was increased by 357.3% (+/−23.2) in the LPS-treated RAW264.7 macrophage cells as compared with the normal RAW264.7 macrophage cells, which were not treated with LPS, but the expression of IL-1β was reduced by 173.1% (+/−8.1) in the RAW264.7 macrophage cells, which were treated with the electromagnetic wave having a wavelength of 0.05 nm or more and 10 nm or less, as compared with the LPS-treated RAW264.7 macrophage cells, exhibiting a remarkable expression reduction effect. Accordingly, it was confirmed that the expression of IL-1β protein, which is an inflammatory factor, was reduced when the cells, in which the inflammatory response was induced, was irradiated with the electromagnetic wave having a wavelength of 0.05 nm or more and 10 nm or less, and as result, the electromagnetic wave having a wavelength of 0.05 nm or more and 10 nm or less has been confirmed to reduce the inflammatory response of the cell.

Real-Time Polymerase Chain Reaction (qPCR)

The cells were divided at 3 groups follow: normal RAW264.7 macrophage cells; the LPS-treated RAW264.7 macrophage cells, and the RAW264.7 macrophage cells, which were irradiated with the electromagnetic wave after the LPS treatment was performed. Total RNA was isolated Raw 264.7 cells group using TRIzol reagent, respectively; Complementary DNA (cDNA) was synthesized from 1 μg of total RNA using a SuperScript III first strand cDNA synthesis kit.

A real-time PCR was performed using SYBR Green PCR Mix on an Applied Biosystems 7500 Fast Real-Time PCR System (Thermo Fisher Scientific Waltham, Mass., USA). The amplification of the cDNA includes initial denaturation at 95° C. for 10 minutes, followed by 40 cycles of denaturation at 95° C. for 10 seconds, annealing at 60° C. for 30 seconds, and extension at 72° C. for 30 seconds. Primers used for the amplification are shown in Table 1 below. Relative mRNA levels were calculated using the 2-ΔΔCt method and normalized to β-actin.

TABLE 1

| Gene Product | Primer Sequence |
| --- | --- |
| Interleukin-1 beta (IL-1β) | Forward:<br>5'-AAGGGCTGCTTCCAAACCTTTGAC-3'<br>Reverse:<br>5'-ATACTGCCTGCCTGAAGCTCTTGT-3' |
| Interleukin-6 (IL-6) | Forward:<br>5'-ATCCAGTTGCCTTCTTGGGACTGA-3'<br>Reverse:<br>5'-TAAGCCTCCGACTTGTGAAGTGGT-3' |
| Tumor necrosis factor-alpha (TNF-α) | Forward:<br>5'-TCTCATGCACCACCATCAAGGACT-3'<br>Reverse:<br>5'-ACCACTCTCCCTTTGCAGAACTCA-3' |
| β-actin | Forward:<br>5'-GGCTGTATTCCCCTCCATC-3'<br>Reverse:<br>5'-ATGCCATGTTCAATGGGGTA-3' |

Figure 3C:
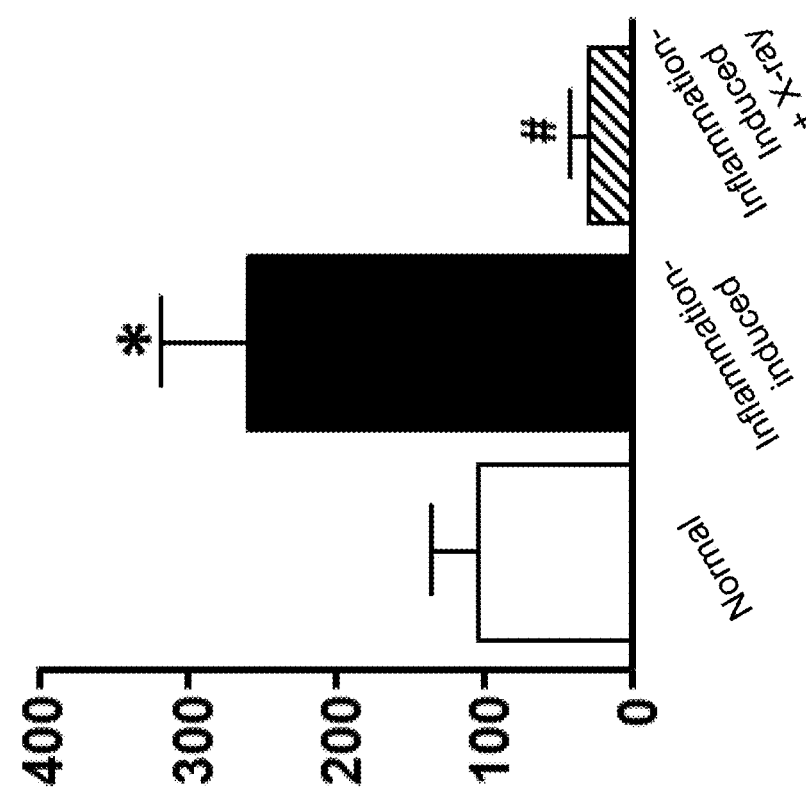
FIGS. 3C to 3E are graphs illustrating the comparison of intracellular expression levels of mRNA expressing IL-1β, IL-6, TNF-α proteins, which are known to exhibit an inflammatory response, using a real-time polymerase chain reaction (PCR).

As a result, as shown in FIG. 3, the level of mRNA expressing IL-1β protein increased by 260% (+/−57.6) in the LPS-treated RAW264.7 macrophage cells as compared with the normal RAW264.7 macrophage cells, but the level of mRNA expressing the IL-1β protein was reduced by 29.2% (+/−11.8) in the RAW264.7 macrophage cells, which were treated with the electromagnetic wave having a wavelength of 0.05 nm or more and 10 nm or less, as compared with the LPS-treated RAW264.7 macrophage cells, exhibiting a remarkably lower mRNA level (FIG. 3C).

Figure 3D:
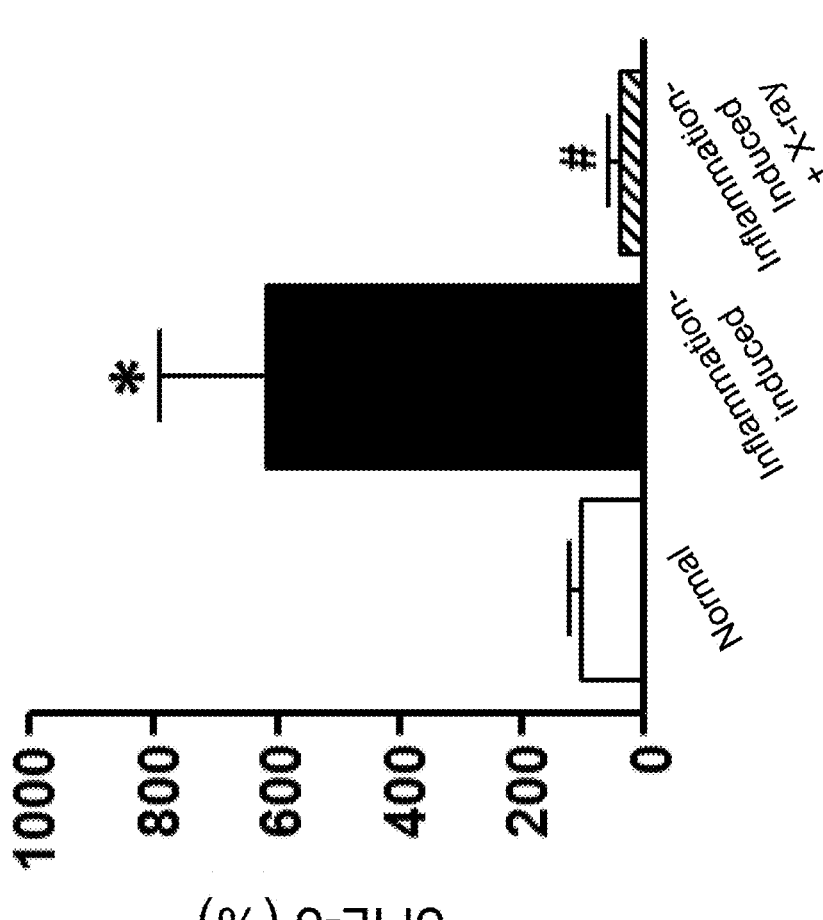
Figure 3E:
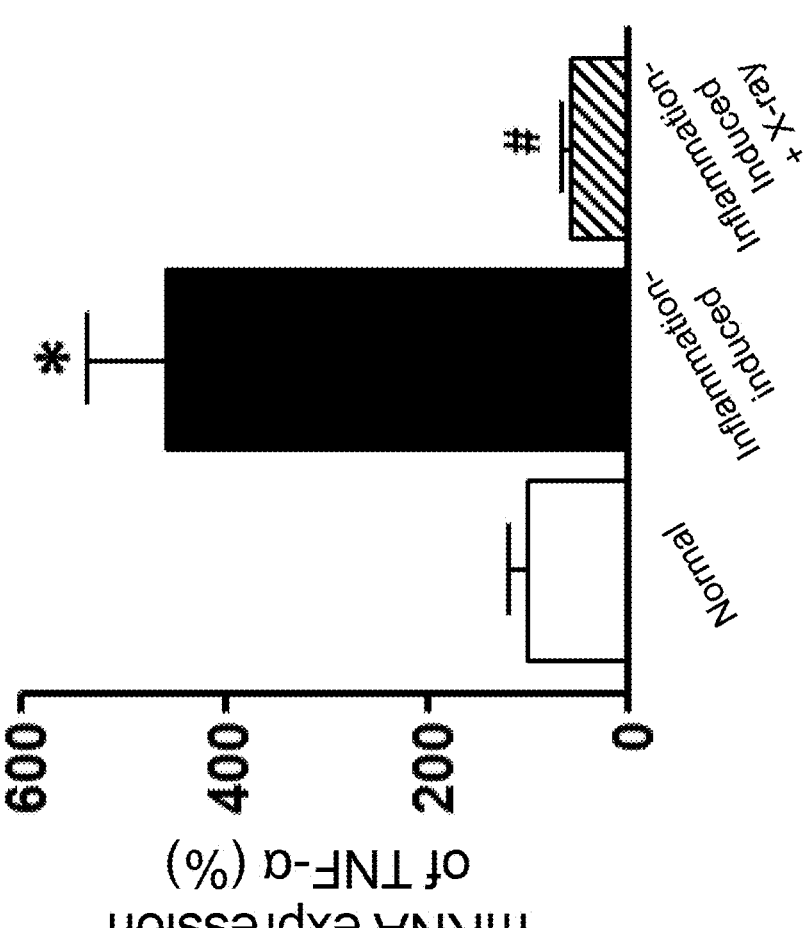

In addition, as shown in FIGS. 3D and 3E, the levels of mRNA expressing IL-6 and TNF-α were increased by 613.1% (+/−175) and 455.4% (+/−80.0), respectively, in the LPS-treated RAW264.7 macrophage cells as compared with the normal RAW264.7 macrophage cells, but the levels of mRNA expressing IL-6 and TNF-α were decreased by 17.4% (+−15.9) and 58.8% (+/−16), respectively, in the RAW264.7 macrophage cells, which were treated with the electromagnetic wave having a wavelength of 0.05 nm or more and 10 nm or less, exhibiting a remarkably lower mRNA level (FIGS. 3D and 3E).

Accordingly, it was confirmed that the level of mRNA expressing IL-1β, IL-6, and TNF-α proteins causing an inflammatory response was remarkably reduced when the electromagnetic wave having a wavelength of 0.05 nm or more and 10 nm or less was irradiated onto the cells in which the inflammatory response was induced, and as result, the electromagnetic wave having a wavelength of 0.05 nm or more and 10 nm or less has been confirmed to reduce the inflammatory response of the cell.

Lipid Accumulation Analysis

RAW264.7 macrophage cells were seeded in tomidish for 24 hours and treated with 500 μM LPS for 3 hours to induce an inflammatory response. Thereafter, the LPS-treated RAW264.7 macrophage cells were irradiated with an electromagnetic wave having a wavelength of 0.05 nm or more and 10 nm or less and an output power of 4.9 W at a distance of 0.07 m for 10 minutes, and then incubated at 37+/−2° C. and in an atmosphere of 5% CO2 for 21 hours without further irradiation of the electromagnetic wave. Thereafter, Live cell images of the normal RAW264.7 macrophage cells, which were not treated with LPS, the LPS-treated RAW264.7 macrophage cells, and the RAW264.7 macrophage cells, which were irradiated with the electromagnetic wave after the LPS treatment was performed, were obtained using a Tomocube HT-1S microscope (Tomocube, Daejeon, Korea). The degree of lipid accumulation in the cell was analyzed on the basis of a three-dimensional (3D) refractive index (RI) distribution of the cell using the Tomostudio software.

Figure 4A:
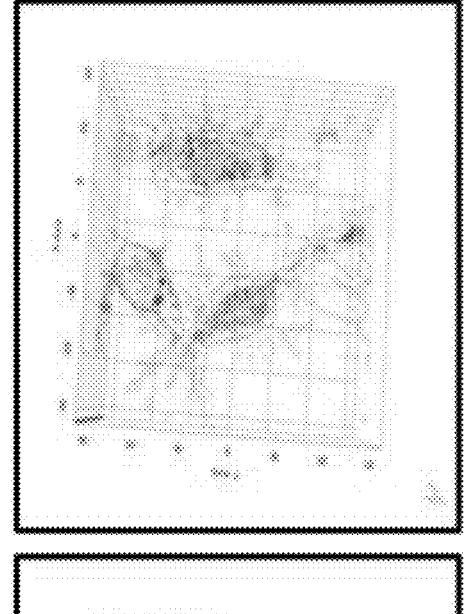
FIG. 4A illustrates images confirming the amount of intracellular lipid accumulation in the normal cells in which the inflammatory response is not induced, the inflammation-induced cells in which the inflammatory response is induced, and the cells in which an electromagnetic wave is irradiated onto the inflammation-induced cells, in which the inflammatory response is induced, with a three-dimensional (3D) hologram.
Figure 4A:
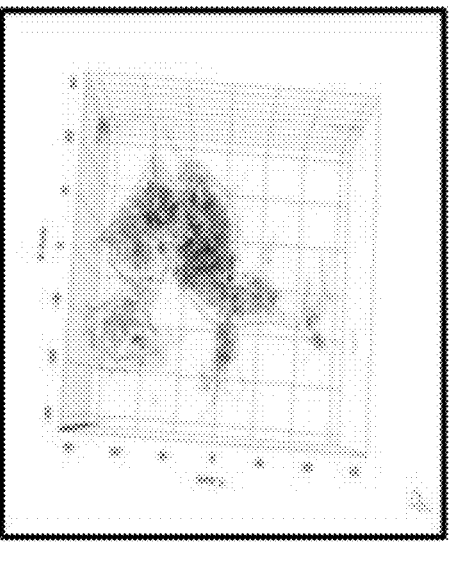
Figure 4A:
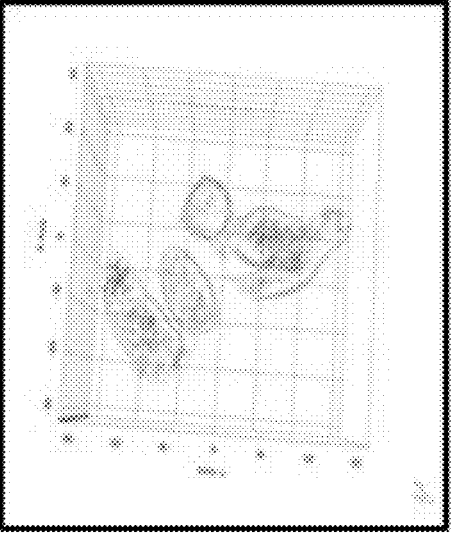
Figure 4B:
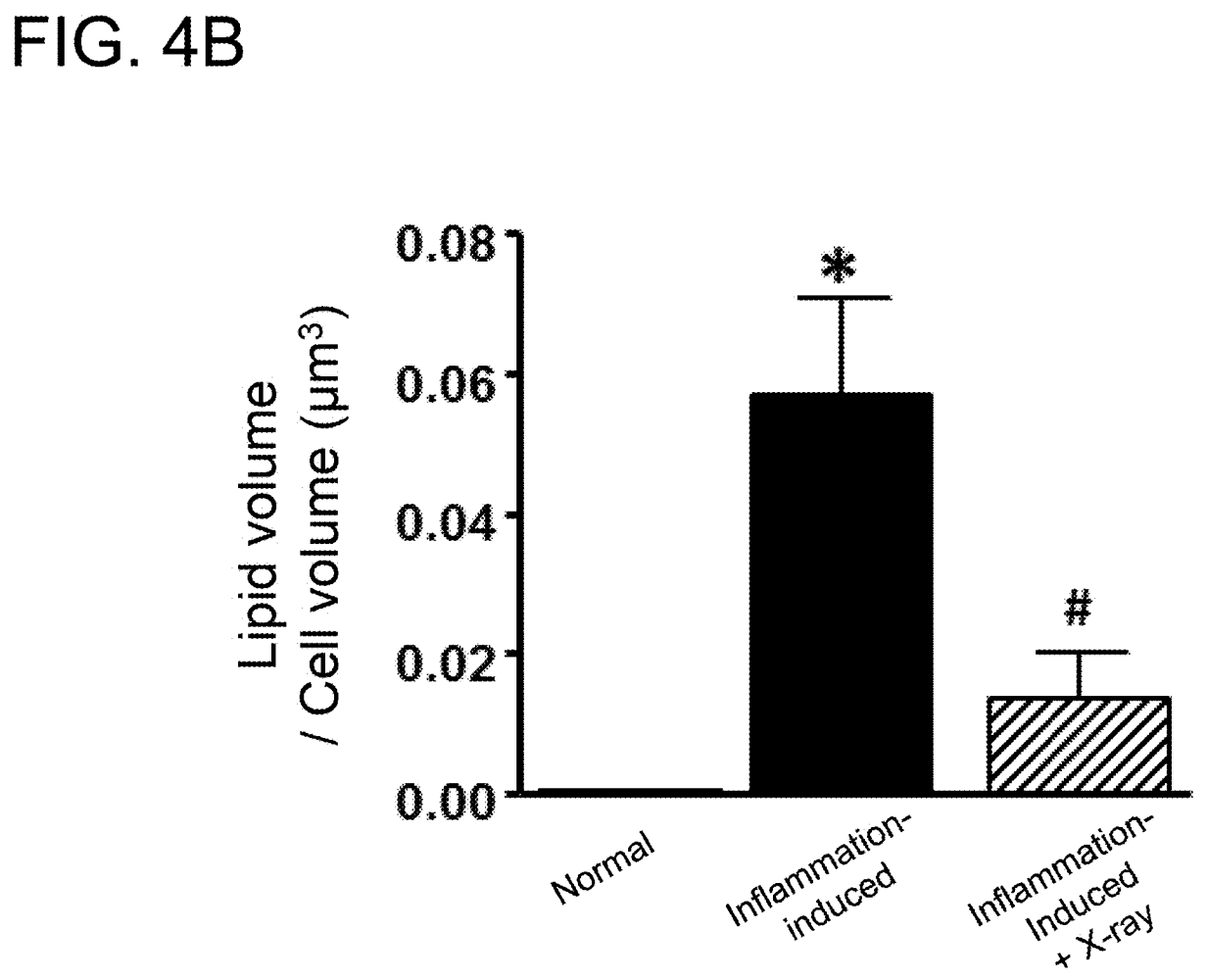

As a result of confirming the amount of lipid droplets accumulated in the cell by 3D hologram analysis, as shown in FIG. 4, it was confirmed that the distribution of lipids was remarkably reduced (FIG. 4A) in the RAW264.7 macrophage cells, which were treated with the electromagnetic wave having a wavelength of 0.05 nm or more and 10 nm or less, as compared with the LPS-treated RAW264.7 macrophage cells, and even when the amount of lipid accumulation was quantitatively compared, it was confirmed that the distribution of lipids was reduced by 0.017% (+/−0.012), and a remarkable decrease in the amount of lipid accumulation was observed (FIG. 4B). Accordingly, it was confirmed that the amount of lipid accumulation in the cells associated with the inflammatory response is remarkably reduced when the electromagnetic wave having a wavelength of 0.05 nm or more and 10 nm or less was irradiated onto the cell in which the inflammatory response was induced, and as a result, it was confirmed that the electromagnetic wave having a wavelength of 0.05 nm or more and 10 nm or less may treat, inhibit, or prevent the inflammatory response.

Example 3

Analysis of Inflammatory Factor in Inflammatory Inducing Animal Model 8-week-old male C5BL/6 mice (Orient Bio Inc., Gyunggido, Korea) were individually housed to allow free access to water and food (based on an AIN-93G formula) in a controlled environment (at room temperature (24+/−2° C. and at humidity of 40±2%) with a 12-hour light/dark cycle. The mice were stabilized for one week, and then, 5 mg/kg of LPS was administered into an abdominal cavity of each mouse, and after 4 hours, some mice were irradiated with an electromagnetic wave having a wavelength of 0.05 nm or more and 10 nm or less and an output power of 4.9 W at a distance of 0.05 m for 10 minutes. After 4 hours of LPS administration, blood was taken from the heart of the mouse, which was not irradiated with the electromagnetic wave, and the mouse irradiated with the electromagnetic wave into a heparin tube.

The expression level of IL-1β, which is an inflammatory cytokine, was confirmed using enzyme-linked immunosorbent assay (ELISA; R&D systems). The obtained mouse plasma sample and 50 μL standard IL-1β-coated supernatant were placed on a 96 well-plate, allowed to react at room temperature, and washed 3 times with 1× wash buffer. 100 μl of conjugate was placed on a 96 well-plate and allowed to react at room temperature for 1 hour, then washed 3 times with 1× wash buffer, and then the substrate was added and allowed to react at room temperature for 30 minutes. After a stop solution was added, a degree of light absorption was measured at a wavelength of 450 nm by a spectrophotometer, and the amount of IL-1β protein was calculated by comparing the degree of light absorption with a control group.

Figure 5:
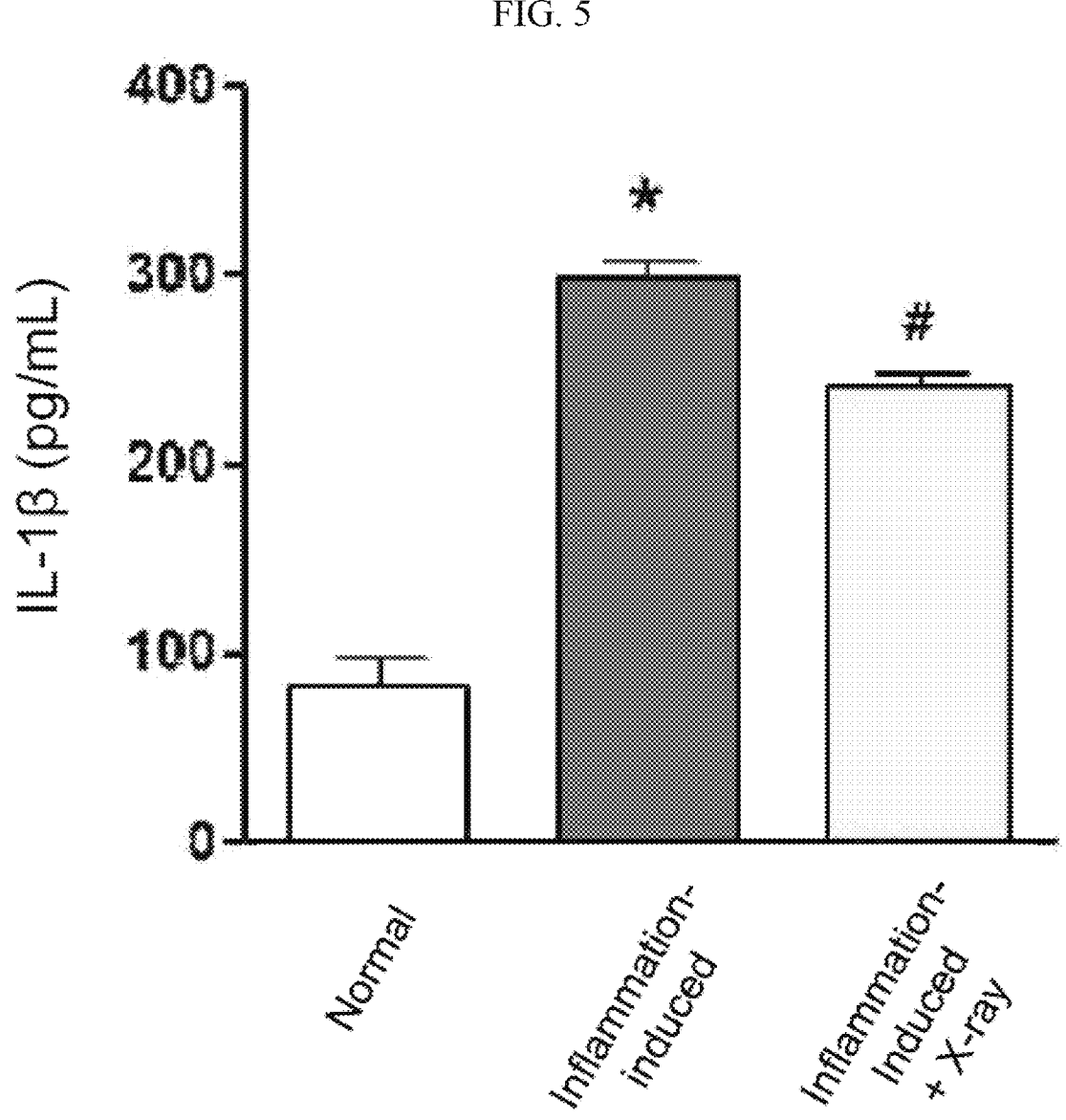
FIG. 5 is a graph illustrating in vivo IL-1β expression levels when an electromagnetic wave is irradiated onto a part other than an affected part of an animal model in which inflammation is induced.

As a result, as shown in FIG. 5, when an electromagnetic wave having a wavelength of 0.05 nm or more and 10 nm or less was irradiated onto the mice treated with LPS to induce inflammation, it may be confirmed that the amount of protein of IL-1β was remarkably reduced as compared with the mice in which inflammation was not induced. Accordingly, it was confirmed that the inflammatory disease may be treated or inhibited even when the electromagnetic wave having a wavelength of 0.05 nm or more and 10 nm or less was directly irradiated onto the animal model.

From the above results, it was confirmed that the amount of factors inducing an inflammatory response may be effectively reduced in the object even when the electromagnetic wave having a wavelength of 0.05 nm or more and 10 nm or less was irradiated onto a part other than the affected part of the object. In other words, it was confirmed that an inflammatory disease may be sufficiently treated, inhibited, or prevented when the electromagnetic wave having a wavelength of 0.05 nm or more and 10 nm or less was irradiated to the whole body of the object, Although the present disclosure has been described with reference to the example embodiments, it should be understood by those skilled in the art that various changes may be made without departing from the spirit and scope of the present disclosure.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An electromagnetic wave treatment apparatus for treating, inhibiting, or preventing an inflammatory disease of an object, comprising:

a power supplier;

an irradiator configured to receive power from the power supplier and irradiate the object with an electromagnetic wave having a wavelength between 0.05 nm and 10 nm; and a controller configured to adjust the wavelength or dose of the electromagnetic wave irradiated from the irradiator, wherein the controller controls the dose of the electromagnetic wave absorbed by the object to be in a range of 1 mGy to 100 mGy per one-time treatment, wherein the irradiator corresponds to a tube including an anode and a cathode, wherein the anode is connected to one side of the power supplier, and the cathode is connected to another side of the power supplier, wherein the cathode comprises an emitter formed of a carbon nanotube (CNT) structure including a plurality of unit yarns each having a structure in which a plurality of CNTs is aggregated and extended in a first direction.

2. The electromagnetic wave treatment apparatus of claim 1, further comprising a filter configured to block the electromagnetic wave having a wavelength of less than 0.05 nm among the electromagnetic wave emitted from the irradiator.

3. The electromagnetic wave treatment apparatus of claim 1, further comprising a protector that surrounds at least a portion of the irradiator.

4. The electromagnetic wave treatment apparatus of claim 1, further comprising a distance measurer configured to measure a distance between a distal end of the irradiator and the object.

5. The electromagnetic wave treatment apparatus of claim 4, further comprising a position adjuster configured to adjust the distance between the distal end of the irradiator and the object.

6. The electromagnetic wave treatment apparatus of claim 5, wherein the controller adjusts the distance between the distal end of the irradiator and the object by controlling the position adjuster on the basis of the distance measured by the distance measurer.

7. The electromagnetic wave treatment apparatus of claim 1, further comprising a collimator configured to adjust an irradiation range or intensity of the electromagnetic wave.

8. The electromagnetic wave treatment apparatus of claim 7, wherein the collimator is controlled by the controller.

9. The electromagnetic wave treatment apparatus of claim 1, wherein the controller controls a voltage or a current supplied to the irradiator from the power supplier.

10. The electromagnetic wave treatment apparatus of claim 1, further comprising a monitoring device configured to display a signal output from the controller.

11. The electromagnetic wave treatment apparatus of claim 1, wherein the electromagnetic wave treatment apparatus is configured to emit the electromagnetic wave directly onto a skin or into a body of the object.

12. The electromagnetic wave treatment apparatus of claim 1, further comprising an applicator connected to the irradiator so that the electromagnetic wave generated by the irradiator is configured to be directly irradiated into a body of the object.

13. The electromagnetic wave treatment apparatus of claim 1, wherein the tube further includes at least one gate, wherein at least one of one side or another side of the controller is connected to the at least one gate.

14. The electromagnetic wave treatment apparatus of claim 1, wherein the inflammatory disease of the object is a disease or lipid storage disorder mediated by a biomarker including at least one of interleukin (IL)-1$\beta$, IL-6, and tumor necrosis factor (TNF)-$\alpha$.

15. The electromagnetic wave treatment apparatus of claim 1, wherein the inflammatory disease of the object is an autoimmune disease or an autoinflammatory disease.

16. A method of operating the electromagnetic wave treatment apparatus of claim 1, the method comprising:

positioning the irradiator such that the electromagnetic wave is irradiated onto the object; and irradiating the electromagnetic wave onto the object from the irradiator.

17. The method of claim 16, wherein the electromagnetic wave treatment apparatus further includes an applicator connected to the irradiator so that the electromagnetic wave generated by the irradiator is directly irradiated into a body of the object, and the method comprises:

inserting the applicator into the body of the object; and irradiating the electromagnetic wave into the body of the object from the irradiator.

18. A method for treating, inhibiting, or preventing an inflammatory disease of an object, the method comprising irradiating the electromagnetic wave, generated by the electromagnetic wave treatment apparatus of claim 1, having a wavelength between 0.05 nm and 10 nm onto the object.

* * * * *